United States Patent [19]
Godbey

[11] Patent Number: 6,086,911
[45] Date of Patent: *Jul. 11, 2000

[54] DRUG DELIVERY DEVICE

[75] Inventor: Kristin J. Godbey, Vadnais Heights, Minn.

[73] Assignee: 3M Innovative Properties Company, St. Paul, Minn.

[ * ] Notice: This patent is subject to a terminal disclaimer.

[21] Appl. No.: 09/091,331

[22] PCT Filed: Dec. 19, 1996

[86] PCT No.: PCT/US96/20201

§ 371 Date: Jun. 16, 1998

§ 102(e) Date: Jun. 16, 1998

[87] PCT Pub. No.: WO97/23206

PCT Pub. Date: Jul. 3, 1997

[51] Int. Cl.[7] ........................................................ A61F 13/02
[52] U.S. Cl. ............................ 424/448; 604/304; 604/307
[58] Field of Search .............................. 424/448; 604/304, 604/307

[56] References Cited

U.S. PATENT DOCUMENTS

| | | |
|---|---|---|
| Re. 24,906 | 12/1960 | Ulrich . |
| 3,949,128 | 4/1976 | Ostermeier . |
| 4,185,100 | 1/1980 | Rovee et al. . |
| 4,393,076 | 7/1983 | Noda et al. . |
| 4,473,584 | 9/1984 | Heckler . |
| 4,477,468 | 10/1984 | Heckler . |
| 4,533,546 | 8/1985 | Kishi et al. . |
| 4,701,470 | 10/1987 | Heckler . |
| 4,704,406 | 11/1987 | Stanislaus et al. . |
| 4,751,087 | 6/1988 | Wick . |
| 4,849,418 | 7/1989 | Lohner et al. . |
| 5,093,133 | 3/1992 | Wisniewski et al. . |
| 5,206,029 | 4/1993 | Brune et al. . |
| 5,230,701 | 7/1993 | Meyer et al. . |
| 5,266,723 | 11/1993 | Hanna et al. . |
| 5,478,567 | 12/1995 | Nakagawa et al. . |

FOREIGN PATENT DOCUMENTS

| | | |
|---|---|---|
| 0091964-A1 | 10/1983 | European Pat. Off. . |
| 0279519-A1 | 8/1988 | European Pat. Off. . |
| 0338291-A1 | 10/1989 | European Pat. Off. . |
| 0513832-A1 | 11/1992 | European Pat. Off. . |
| 2698787 | 6/1994 | France . |
| 86/02264 | 4/1986 | WIPO . |
| 91/06295 | 5/1991 | WIPO . |
| 91/17740 | 11/1991 | WIPO . |
| 93/08795 | 5/1993 | WIPO . |
| 94/23713 | 10/1994 | WIPO . |
| 95/18603 | 7/1995 | WIPO . |

*Primary Examiner*—Michael A. Williamson
*Attorney, Agent, or Firm*—MarySusan Howard; Ted K. Ringsred; Robert W. Sprague

[57] ABSTRACT

Optically pure S(+) flurbiprofen, which is substantially free of the R(−) enantiomer, is a potent analgesic for relieving pain and inflammation in humans and animals. A method and composition is disclosed utilizing the optically pure S(+) enantiomer of flurbiprofen for treating pain and inflammation.

10 Claims, No Drawings

DRUG DELIVERY DEVICE

BACKGROUND OF THE INVENTION

The present invention relates to drug delivery devices, in particular to transmucosal or transdermal drug delivery devices comprising a flexible backing.

Drug delivery devices for use in the present invention are designed to deliver a therapeutically effective amount of drug to the skin of a patient, e.g., to cure a skin irritation, to deliver a therapeutically effective amount of drug across the skin of a patient (transdermal drug delivery device) or across a mucous membrane of a patient (transmucosal drug delivery device). The present invention is particularly concerned with transdermal drug delivery devices but can equally well be applied to other drug delivery devices in particular transmucosal drug delivery devices. Delivery of drugs across the skin and/or mucosa avoids hepatic first-pass inactivation, poor or erratic absorption from the gastrointestinal tract, and inactivation by gastro-intestinal fluids.

Transdermal drug delivery devices typically involve a carrier (such as a liquid, gel, or solid matrix, or a pressure sensitive adhesive) into which the drug to be delivered is incorporated. Devices known to the art include reservoir type devices involving membranes that control the rate of drug release to the skin and devices involving a dispersion or solution of the drug in a matrix such as a pressure sensitive adhesive. The skin, however, presents a substantial barrier to ingress of foreign substances into the body. It is therefore often desirable or necessary to incorporate excipients into the carrier that enhance the rate at which the drug passes through the skin.

Typically the portions of the carrier that are not in contact with the skin or mucosa are covered by a backing. The backing serves to protect the carrier and the components contained in the carrier, including the drug, from the environment. It is often desirable that the backing have a relatively high vapor transmission rate, since this results in the reduction of moisture buildup on the skin beneath the device and in a corresponding reduction in the amount of skin maceration that occurs. It is also often desirable to have a conformable backing since a stiff backing may cause mechanical irritation. In order to maintain the health of the covered skin during long term wear (e.g., for periods in excess of a day), it is also desirable that the backing have a relatively high permeability to oxygen. Further, as the backing is in contact with the components of the carrier, including the drug and any excipients, it is important that the backing be stable to such components in order that the backing retains its structural integrity and conformability. It is also important that the backing not absorb the drug or excipients from the carrier. In connection with the preparation of certain reservoir type drug delivery devices, it is also desirable for the backing to be heat sealable at a relatively low temperature to a variety of other polymeric substrates.

Backings that have found use in drug delivery devices include metal foils, metalized plastic films, and single layered and multilayered polymeric films. Deficiencies that are sometimes seen with these backings include the delamination of multilayer films; the oxygen impermeability of metal foils, metalized plastic films and certain polymeric films; the low rate of moisture vapor transmission of metal foils, metalized plastic films and certain polymeric films; undue stiffness and lack of conformability of metal foils, metalized plastic films and certain polymeric films; instability of certain polymeric materials to the components of the carrier; and absorption of components from the carrier by certain polymeric materials. Accordingly, there is a substantial need for a backing material that addresses some or all of the above problems.

SUMMARY OF THE INVENTION

The present invention provides a drug delivery device comprising a flexible backing having on at least one part of one surface thereof a carrier comprising a drug, said flexible backing comprising a nonwoven thermoplastic polymer web having multidirectional elasticity comprising substantially continuous and randomly deposited, molecularly oriented fibers of thermoplastic polymer bonded together at intermittent regularly patterned areas throughout the web with unbonded spans of fibers between the bond areas, the fibers being heat set in an undulating configuration with respect to the basic plane of the web to form a series of repeating crests and valleys in the machine direction which flatten into the basic plane on strain induced elongation of the web in the machine direction and reassume their undulated configuration on strain release to provide substantially complete elastic recovery in the machine direction up to at least about 10% strain, the web also containing unbonded spans of fibers disposed in non-linear, buckled configuration with respect to the cross direction in the basic plane and heat set therein such that, on strain induced elongation up to at least about 10% in the cross direction, fibers align in the cross direction and, on strain release, substantially spontaneously reassume their non-linear, buckled configuration, the regularly patterned areas occupying less than about 50% of the surface area of the web and distributed in a density of about 8–490/cm$^2$.

The backings of the present invention avoid the above mentioned deficiencies of the various prior art backings. For example, they generally are permeable to oxygen, have a high vapor transmission rate, and are conformable; these properties decrease the likelihood that the drug delivery device will cause skin irritation. Additionally they are inert to many commonly used excipients and can be heat sealed.

DETAILED DESCRIPTION OF THE INVENTION

A backing material in accordance with the present invention can be produced using the procedure set forth in U.S. Pat. No. 3,949,128, the disclosure of which is incorporated herein by reference. Briefly, the process comprises the steps of providing elasticity in the cross-direction to a suitably bonded web, e.g., a spot-bonded web of thermoplastic polymer, and subsequently providing elasticity in the machine direction of the web.

To provide elasticity in the cross-direction, a spot-bonded web of thermoplastic polymer is heated above its softening point and subsequently drawn in the machine direction by setting the speed of unwinding of the web lower than the speed of winding up of the web. This provides a tension to the web in the machine direction and will cause stretching in that direction. As a consequence, the polymer fibers will assume a non-linear configuration with respect to the cross-direction of the web, i.e., the direction normal to the machine direction. In other words, after drawing of the web, substantially no straight line fiber segments exist between spot bonds in the cross-direction. Additionally, fibers will assume a non-linear configuration by buckling out of the basic plane of the web which results in a lofty surface feel of the material. Buckling of the fibers between spot bond areas is accompanied by movement of the spot bond areas into closer relationship in the cross direction. The capacity for the bond areas to so move on drawing in the machine direction achieves maximum non-linearity of the fibers in the cross direction.

Subsequent to drawing of the thermoplastic polymer web in the machine direction, it is subjected to microcreping. The microcreping process is a mechanical way to impart stretch to a web. A suitable apparatus for microcreping is, e.g., MICROCREPER® (available from MICREX Corp. Walpole, Mass., USA). In the process the web, supported by a main roll, is introduced into a converging passage, firmly gripped, and conveyed into the main treatment cavity where the microcreping process takes place. By adjustment of controls, varying amounts of residual compaction and crepe cross-section can be attained. The treated web passes through a secondary passage between rigid and/or flexible retarders which control the uniformity and degree of compaction. Compaction is retained in the web by annealing the fibers in the compacted state. By "annealing" is meant the maintenance of the fiber at a specified temperature for a specific length of time and the cooling the fiber. This treatment removes internal stresses resulting from the previous microcreping operation and effectively "sets" the web structure in a new orientation. This can be done using dry heat (e.g., hot roll, infrared irradiation, convection oven) or steam. The choice of annealing method depends on such factors as the web weight, fiber type and process speed. One simple method to apply heat to the web is to pass the web over a heated roll. The resulting web has elasticity in the machine direction due to buckling of fibers out of the basic plane of the material in an undulating fashion of crests and valleys thus positioning fibers in a non-linear configuration with respect to the machine direction.

It should be noted that the extent of microcreping need not be uniform across the width of the web. Patterns or decorative designs may be employed using differential compaction delivered by properly designed retarders.

In a particularly preferred embodiment in of the present invention, the web is calendered on conventional equipment subsequent to the microcreping operation. This calendering is preferably performed at a temperature above the softening point of the web with either a small (about 1.5 mm$^2$) waffle patterned or a smooth rubber top roll and a smooth chrome bottom roll set apart by a gap adjusted to hold the web against the heated bottom roll without crushing or otherwise substantially affecting the elasticity of the web to produce a smoother surface on one side of the web for lamination of the carrier comprising the drug while retaining the multidirectional stretch properties of the web.

The surface of the web that is to be laminated to the carrier may also be corona treated to enhance the bonding of the carrier, particularly a drug-in-adhesive matrix, to the web. Further, the surface of the web that is opposite to the surface containing the carrier with the drug, may be treated with an agent such as a fluorocarbon to impart water repellency to the web.

Preferred webs, although stretchable, are not overly elastic. Webs, which are overly elastic, when used as backings for transdermal drug delivery devices, have a tendency to try to return to the original flat shape when applied over a joint such as an elbow. This tendency can cause the edges of the patch to lift and exacerbate any mechanical irritation which may be present.

Some suitable thermoplastic polymers for use in the non-woven web in connection with the present invention include, e.g., polyolefin polymers such as for example polyethylene and polypropylene and polyesters such as, e.g., polyethyleneterephthalate.

A highly preferred backing for use in the present invention comprises polypropylene fibers and is preferably prepared as follows.

A spunbonded polypropylene nonwoven web with an offset intermittent spot welded structure and a basis weight of a nominal 60 grams per square meter (available as LUTRASIL® LS-4460 from Freudenberg Spunweb Co.) is heated (about 138° C.) and stretched under tension (accomplished by adjusting the unwind and wind-up tensions or speeds to produce a 1:1.5 (±0.1) differential) using conventional equipment in a process known as "necking down" or "stretch-setting". This process reduces the width of the web, increases the length of the web and imparts a stretch in the cross-web direction. The "necked down" web is then microcreped using a MICROCREPER™ (available from the MICREX Corp., Walpole, Mass., USA) with compression ratios from 30% to 40% and a temperature set at 70° C., This process imparts a stretch in the down-web or machine direction. The resulting multidirectional stretch web is calendered on conventional equipment at a temperature of about 138° C. and a pressure of 100 psi (7.0 Kg/cm$^2$) using a smooth rubber top roll and a smooth chrome bottom roll with a set gap of 0.005" (0.0127 cm) to produce a smoother surface for lamination of the drug-in-adhesive matrix while retaining the multidirectional stretch properties.

As can be appreciated from the above, the webs are produced without chemical treatments. Accordingly, there is little risk of introducing toxic components into a (transdermal) drug delivery device. The webs are heat sealable and may therefore be used in the fabrication of reservoir type devices in addition to drug-in-adhesive devices. The multidirectional elasticity of these webs allows drug delivery devices employing them as backings to be comfortably worn, particularly in the case of a transdermal drug delivery device worn over joints such as elbows and knees.

A drug delivery device of the invention can be prepared by using conventional methods to apply an appropriate carrier to the backing. For example, a drug-in-adhesive device can be prepared by using the following method; preparing a coating formulation by mixing a solution of the adhesive in a solvent with the drug and any excipients to form a homogeneous solution or suspension; applying the formulation to a substrate (a backing or a release liner) using well known knife or bar or extrusion die coating methods; drying the coated substrate to remove the solvent; and laminating the exposed surface to a release liner or backing. The term "carrier" as used herein refers generally to any element suitable for containing drug and releasing the drug to the skin or mucosa. A carrier generally has a surface adapted to be applied to the skin or mucosa and an opposing surface adapted to be applied to a backing. In a preferred embodiment of the present invention the carrier comprises an adhesive composition having the drug(s) dispersed or dissolved therein. In a particularly preferred embodiment of the present invention the adhesive composition comprises a pressure sensitive adhesive.

As used herein, the term "pressure-sensitive adhesive" refers to a viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives. The term pressure-sensitive adhesive also includes mixtures of different polymers and mixtures of polymers, such as polyisobutylenes (PIB) of different molecular weights, the resultant mixture being a pressure-sensitive adhesive.

In preferred embodiments of the invention, the adhesive composition comprises a polyacrylate. The polyacrylate can be a homopolymer or copolymers of various acrylate and/or methacrylate esters. The adhesive may also include copolymerizable monomers such as those containing functional groups in addition to an ethylenically unsaturated group. By varying the amount of each type of monomer added, the cohesive properties of the resulting adhesive can be adjusted as is known in the art.

Suitable acrylate adhesives are known in the art and some are commercially available, including the adhesives sold under the trademarks Duro-Tak 80-1194, 80-1196, 80-1197, 2287, 2516 and 2852 by National Starch and Chemical Corporation, Bridgewater, N.J. Other suitable acrylate adhesives are those sold under the trademarks Gelva-Multipolymer Solution GMS 737, 788, 1151 and 1430 (Monsanto; St. Louis, Mo.).

Other polymers can be blended with the polyacrylate. For example, rubber adhesives may be blended with the polyacrylate.

Additional adhesives useful in practicing the invention include natural and synthetic polyisoprene, polybutylene, polyisobutylene, styrene/butadiene polymers, styrene-isoprene-styrene block copolymers, butyl rubber, polyacrylonitrile, polytetrafluoroethylene, polyvinylchloride, polyvinylidene chloride, polysiloxanes and other copolymers thereof As used herein, the term "drug," includes its equivalents, "bioactive agent," and "medicament" and is intended to have the broadest meaning as including substances intended for use in the diagnosis, cure, mitigation, treatment or prevention of disease, or to affect the structure or function of the body.

Exemplary drugs that can be included in the carrier include substances capable of local or systemic effect when administered to the skin or mucosa, such as clonidine, estradiol, nicotine, nitroglycerin, and scopolamine, all of which are commercially available in the form of transdermal delivery devices. Others include antiinflammatory drugs, both steroidal (e.g., hydrocortisone, prednisolone, triamcinolone) and nonsteroidal (e.g., naproxen, piroxicam); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators (e.g., nitroglycerin); calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone, testosterone, estradiol, levonorgestrel); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinoline-4-amine, and other compounds disclosed in U.S. Pat. No. 4,689,338, incorporated herein by reference, acyclovir); local anesthetics (e.g., benzocaine, propofol); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl); peptide hormones (e.g., human or animal growth hormones, LHRH); cardioactive products such as atriopeptides; proteinaceous products (e.g., insulin); enzymes (e.g., anti-plaque enzymes, lysozyme, dextranase); antinauseants (e.g., scopolomine); anticonvulsants (e.g., carbamazine); immunosuppressives (e.g., cyclosporine); psychotherapeutics (e.g., diazepam); sedatives (e.g., phenobarbital); anticoagulants (e.g., heparin); analgesics (e.g., acetaminophen); antimigraine agents (e.g., ergotamine, melatonin, sumatriptan); antiarrhythmic agents (e.g., flecainide); antiemetics (e.g., metaclopromide, ondansetron); anticancer agents (e.g., methotrexate); neurologic agents such as anxiolytic drugs; hemostatics; anti-obesity agents; and the like, as well as pharmaceutically acceptable salts, esters, solvates and clathrates thereof.

The drug is present in a drug delivery device of the invention in a therapeutically effective amount, i.e., an amount effective to bring about a desired therapeutic result in the treatment of a condition. The amount that constitutes a therapeutically effective amount varies according to the particular drug incorporated in the device, the condition being treated, any drugs being coadministered with the selected drug, desired duration of treatment, the surface area of the skin or mucosa over which the device is to be placed, and other components of the drug delivery device.

The carrier of the drug delivery system can also contain agents known to accelerate the delivery of the drug through the skin or mucosa. These agents have been referred to as penetration enhancers, accelerants, adjuvants, and sorption promoters, and are collectively referred to herein as "enhancers". Some examples of enhancers are polyhydric alcohols such as dipropylene glycol, propylene glycol, and polyethylene glycol; oils such as olive oil, squalene, and lanolin; polyethylene glycol ethers and fatty ethers such as cetyl ether and oleyl ether; fatty acid esters such as isopropyl myristate; fatty acid alcohols such as oleyl alcohol; urea and urea derivatives such as allantoin; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide; salicylic acid; amino acids; benzyl nicotinate; bile salts; and higher molecular weight aliphatic surfactants such as lauryl sulfate salts. Other agents include oleic and linoleic acids, ascorbic acid, panthenol, butylated hydroxytoluene, tocopherol, tocopheryl acetate, tocopheryl linoleate, propyloleate, isopropyl palmitate, oleamide, polyoxyethylene (4) lauryl ether, polyoxyethylene (2) oleyl ether and polyoxyethylene (10) oleyl ether sold under the trademarks Brij 30, 93 and 97 by ICI Americas, Inc., and polysorbate 20 sold under the trademark Tween 20 by ICI Americas, Inc.

Further a plasticizer or tackifying agent can be incorporated into the adhesive composition to improve the adhesive characteristics of the adhesive composition. A tackifying agent is particularly useful in those embodiments in which the drug and/or any excipient does not plasticize the polymer. Suitable tackifying agents are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and 7) hydrogenated wood resins or rosins. The tackifying agent employed is preferably compatible with the blend of polymers. Silicone fluid is useful for blends comprising polysiloxane as a major component. In other embodiments, where a synthetic rubber, for example, is a major component, mineral oil is a preferred tackifying agent. Acrylate adhesives can be tackified with oleates, oleic acid, oleyl alcohol and other fatty acid-derived agents.

Some drugs, such as the vasodilator nitroglycerin, function as plasticizers in the adhesive because they are soluble to a certain degree in the polymers comprising the adhesive. For drug molecules which are not readily soluble in the polymer system, a co-solvent for the drug can be added. Co-solvents, such as lecithin, retinol derivatives, tocopherol, dipropylene glycol, triacetin, propylene glycol, saturated and unsaturated fatty acids, mineral oil, silicone fluid, alcohols, butyl benzyl phthalate, and the like are useful depending on the solubility of the drug in the adhesive carrier.

In one exemplary preferred embodiment, this invention provides a transdermal delivery device comprising:

(A) the above defined backing;
(B) an adhesive layer adhered to one surface of the backing and comprising a mixture of
  (1) a copolymer comprising interpolymerized units derived from
    (a) one or more A monomers selected from the group consisting of alkyl acrylates containing 4 to 10 carbon atoms in the alkyl group and alkyl methacrylates containing 4 to 10 carbon atoms in the alkyl group; and
    (b) one or more ethylenically unsaturated B monomers comprising a functional group selected from the group consisting of carboxylic acid, sulfonamide, urea, carbamate, carboxamide, hydroxy, amino, oxy, oxo and cyano;
  (2) flurbiprofen in a therapeutically effective amount;
  (3) isopropyl myristate in an amount of about 20 to about 40 percent by weight based on the total weight of the adhesive layer; and
  (4) polyvinylpyrrolidone in an amount of about 1 to about 40 percent by weight based on the total weight of the adhesive layer, wherein the backing and adhesive layer together has a moisture vapor transmission rate greater than 400 $g/m^2/24$ hr. Preferably the adhesive layer mixture is homogeneous.

In a particularly preferred embodiment, this invention provides transdermal delivery devices containing flurbiprofen, especially S(+)-flurbiprofen. Generally, flurbiprofen is present in an amount by weight of about 1 to about 25 percent, preferably about 5 to 15 percent, by weight based on the total weight of the adhesive layer. In a preferred embodiment the adhesive layer is substantially free of solid undissolved flurbiprofen.

The flurbiprofen transdermal delivery device further comprises isopropyl myristate in the adhesive layer in an amount by weight of about 20 to 40 percent, preferably 25 to 35 percent, based on the total weight of the adhesive layer. The isopropyl myristate generally is dispersed or preferably dissolved in the adhesive layer and enhances flurbiprofen penetration through the skin when this phenomenon is measured using the skin penetration test method described below.

The copolymer used in the flurbiprofen transdermal delivery device preferably is substantially chemically inert to both flurbiprofen and to isopropyl myristate. The inherent viscosity of the copolymer is such as to ultimately provide a suitable pressure sensitive adhesive when used in a device of the invention. Preferably the copolymer has an inherent viscosity in the range 0.2 dl/g to about 2 dl/g, more preferably 0.3 dl/g to about 1.4 dl/g.

Suitable copolymers for use in the adhesive layer of the flurbiprofen transdermal delivery device preferably comprise about 80 to 95 percent by weight, more preferably 88 to 94 percent by weight, based on the total weight of the copolymer, of interpolymerized units derived from one or more A monomers selected from the group consisting of alkyl acrylates containing 4 to 10 carbon atoms in the alkyl group and alkyl methacrylates containing 4 to 10 carbon atoms in the alkyl group. Examples of suitable alkyl acrylates and methacrylates are n-butyl, n-pentyl, n-hexyl, cyclohexyl, isoheptyl, n-nonyl, n-decyl, isohexyl, isobornyl, 2-ethyloctyl, isooctyl, and 2-ethylhexyl acrylates and methacrylates. Preferred alkyl acrylates include isooctyl acrylate, 2-ethylhexyl acrylate, n-butyl acrylate and cyclohexyl acrylate. A particularly preferred alkyl acrylate is isooctyl acrylate. Particularly preferred alkyl methacrylates include butyl methacrylate, cyclohexyl methacrylate, and isobornyl methacrylate.

The copolymer component of the adhesive layer further comprises interpolymerized units derived from one or more ethylenically unsaturated B monomers, preferably in a total amount from about 5 to 20 percent by weight, more preferably 6 to 12 percent by weight, based on the total weight of the copolymer. Suitable B monomers include those comprising a functional group selected from the group consisting of carboxylic acid, sulfonamide, urea, carbamate, carboxamide, hydroxy, amino, oxy, oxo, and cyano. Exemplary B monomers include acrylic acid, methacrylic acid, maleic acid, a hydroxyalkyl acrylate containing 2 to 4 carbon atoms in the hydroxyalkyl group, a hydroxyalkyl methacrylate containing 2 to 4 carbon atoms in the hydroxyalkyl group, acrylamide, methacrylamide, an alkyl substituted acrylamide containing 1 to 8 carbon atoms in the alkyl group, N-vinyl-N-methyl acetamide, N-vinyl valerolactam, N-vinyl caprolactam, N-vinyl-2-pyrrolidone, glycidyl methacrylate, vinyl acetate, alkoxyethyl acrylate containing 1 to 4 carbon atoms in the alkoxy group, alkoxyethyl methacrylate containing 1 to 4 carbon atoms in the alkoxy group, 2-ethoxyethoxyethyl acrylate, furfuryl acrylate, furfuryl methacrylate, tetrahydrofurfuryl acrylate, tetrahydrofurfuryl methacrylate, propylene glycol monomethacrylate, propylene oxide methyl ether acrylate, di(lower)alkylamino ethyl acrylate, di(lower)alkylamino ethyl methacrylate, di(lower alkyl)aminopropyl methacrylamide, acrylonitrile, and methacrylonitrile. Preferred B monomers include N,N-dimethylacrylamide, acrylamide and acrylic acid.

The above described copolymers are known, and methods of preparation are well known to those skilled in the art, having been described for example in U.S. Pat. No. RE 24,906 (Ulrich), the disclosure of which is incorporated herein by reference.

The adhesive layer further comprises polyvinylpyrrolidone (PVP). As used herein, the term "polyvinylpyrrolidone" means either a homopolymer of N-vinyl-2-pyrrolidone or a copolymer comprising interpolymerised units derived from N-vinyl-2-pyrrolidone and these units are present in an amount by weight of more than 50 percent based on the total weight of the copolymer. Examples of suitable PVP homopolymers and copolymers are those meeting the specifications set forth in the European Pharmacopoeia monographs for "polyvidone" and "copolyvidonum". Such polyvinylpyrrolidones are available under the tradename KOLLIDON from BASF AG. Preferred PVP homopolymers are Kollidon 25, Kollidon 30 and Kollidon 90. A preferred PVP copolymer is Kollidon VA 64 which is a copolymer of N-vinyl-2-pyrrolidone and vinylacetate. The polyvinylpyrrolidone is present in the adhesive layer in an amount by weight of about 1 to 10 percent, more preferably 3 to 8 percent by weight, based on the total weight of the adhesive layer. The incorporation of the PVP into the adhesive layer serves to lower the tack and to increase the cohesive strength of the adhesive layer. If the tack is too high, removal of the device from skin can be painful. If the cohesive strength is too low, then an unacceptable amount of adhesive residue may be left on the skin when the device is removed.

A flurbiprofen-containing transdermal delivery device of the present invention can be prepared by combining the copolymer, isopropyl myristate and the flurbiprofen in an organic solvent (e.g., ethyl acetate) with a solution containing polyvinylpyrrolidone in an organic solvent (e.g., isopropanol) to afford a coating formulation. The coating formulation can be coated using conventional methods onto a suitable release liner to provide a predetermined uniform thickness of the coating formulation. Suitable release liners include conventional release liners comprising a known sheet material such as a polyester web, polyethylene web, or a polystyrene web, or a polyethylene-coated paper coated with a suitable fluoropolymer or silicone based coating. The coated release liner is oven dried and then laminated onto the backing material of the present invention using conventional methods.

The flurbiprofen-containing transdermal delivery devices, as well as other transdermal delivery devices in accordance with the invention can be made in the form of an article such as a tape, a patch, a sheet, a dressing or any other form known to those skilled in the art. Generally the device will be in the form of a patch of a size suitable to deliver a preselected amount of flurbiprofen or other drug through the skin.

A flurbiprofen-containing device in accordance with this invention may be used to treat any condition capable of treatment with flurbiprofen, e.g., pain and inflammation associated with arthritis and soft tissue injury. The device can be placed on the skin and allowed to remain for a time sufficient to achieve or maintain the intended therapeutic effect. The time that constitutes a sufficient time can be selected by those skilled in the art with consideration of the flux rate of the device of the invention and of the condition being treated.

The example set forth below is intended to illustrate the invention.

In Vitro Skin Penetration Test Method

The skin penetration data given below was obtained using the following test method. A diffusion cell is used. Hairless mouse skin (female hairless mice, 3–4 weeks old) or human cadaver skin is used. The skin is mounted epidermal side up between the upper and the lower portion of the cell, which are held together by means of a ball joint clamp.

The portion of the cell below the mounted skin is completely filled with receptor fluid "HEPES" (N-[2-hydroxyethyl]piperazine-N'-[2-ethanesulfonic acid]) buffered Hanks balanced salt solution, pH 7.2, supplemented with 1.5 mmolar sodium azide such that the receptor fluid is in contact with the skin. The receptor fluid is stirred using a magnetic stir bar. The sampling port is covered except when in use.

When a transdermal delivery device is evaluated, the skin is placed across the orifice of the lower portion of the diffusion cell, the release liner is removed from a 1.55 cm² patch and the patch is applied to the skin and pressed to cause uniform contact with the skin. The diffusion cell is assembled and the lower portion is filled with receptor fluid.

The cell is then placed in a constant temperature (32±1.5° C.) and humidity (45±5% relative humidity) chamber. The receptor fluid is stirred by means of a magnetic stirrer throughout the experiment to assure a uniform sample and a reduced diffusion barrier on the dermal side of the skin. The entire volume of receptor fluid is withdrawn at specified time intervals (3, 6, 9, 12, 24, 36 and 48 hours) and immediately replaced with fresh fluid. The withdrawn fluid is analyzed for drug content using conventional high performance liquid chromatography. The cumulative amount of S(+)-flurbiprofen penetrating the skin is calculated.

Moisture Vapor Transmission Rate Test Method

The Moisture Vapor Transmission Rate (MVTR) data given below was obtained using the following test method. This test method is a modified version of ASTM E 96-80.

A sample having a diameter of 31 mm is die cut from the laminate being tested. An adhesive-backed foil ring having an inner diameter ("i.d.") of 24.4 mm and an outer diameter ("o.d.") of 37.5 mm is laminated to the backing surface of the test sample. The release liner is removed from the test sample and a second adhesive-backed foil ring (i.d. 24.4 mm; o.d. 37.5 mm) is laminated to the adhesive surface of the test sample such that the two foil rings are concentrically aligned and the test sample is sandwiched between the adhesive surfaces of the foil rings. The resulting foil/sample/foil laminate is smoothed to remove any wrinkles or voids.

A brown glass jar (100 mL) having a 40 mm diameter opening is half-filled with 50 mL of distilled water. The jar is fitted with a screw-on lid having a 30 mm diameter hole.

The foil/sample/foil laminate is concentrically positioned in the lid such that the adhesive surface of the sample will be facing the interior of the jar when the lid is screwed onto the jar. A gasket having an inner diameter of 30 mm is inserted into the lid and the resulting lid/laminate/gasket sub-assembly is screwed loosely onto the jar.

The assembly is placed into a chamber maintained at a temperature of 40° C. and 20% relative humidity. The assembly is removed from the chamber after 4 hours and weighed to the nearest 0.01 g ($W_1$). The lid is screwed tightly onto the jar and the assembly is returned to the chamber. After 24 hours the assembly is removed from the chamber and weighed to the nearest 0.01 g ($W_2$).

The MVTR of the sample (measured in grams of water transmitted per square meter of sample area over a 24 hour period) may then be calculated according to the following equation:

$$MVTR = \frac{(W_1 - W_2)}{4.676} \times 10000$$

Six (6) samples of each laminate are run and the average of the 6 samples is reported.

180 Degree Peel Adhesion to Stainless Steel

The values given below for 180 degree peel adhesion to stainless steel were obtained using a modified version of ASTM D 3330-90.

A 2.54 cm by 7.62 cm sample is die cut from the laminate being tested. The release liner is peeled down 1 cm and the exposed adhesive surface is adhered to a leader strip. (If a coated release liner is being used as a leader then the adhesive surface should be attached to the uncoated side.) The release liner is removed from the test sample. The test sample is positioned adhesive side down, lengthwise with and approximately in the center of the stainless steel test surface (a 5 cm by 14 cm stainless steel plate that has been washed once with 4-hydroxy-4-methyl-2-pentanone and three times with acetone or ethyl acetate). The sample is rolled down using one forward and one reverse pass with a 2 Kg roller moved at a rate of approximately 6 mm/sec. The sample is then allowed to stand at ambient temperature for 15 minutes. The peel force required to remove the tape at 180 degree angle is measured using an appropriate piece of test equipment (e.g., Frank Universalprüfmaschine 81565 or Instron machine 4201). The rate of removal is 230 mm/min. The force of removal is reported in Newtons. Ten (10) samples of each laminate are run and the average of the 10 samples is reported.

Preparation of Isooctyl Acrylate/Acrylic Acid (90/10) Copolymer

A flask equipped with an agitator, condenser, nitrogen inlet tube and an addition funnel was charged with isooctyl acrylate (72.0 g), acrylic acid (8.0 g) and ethyl acetate (78.1 g). The mixture was heated to 60° C. with medium agitation and purged with nitrogen to remove oxygen. Lucidol 75 (0.07 g, available from Elf Atochem North America) premixed in ethyl acetate (3.0 g) was added to initiate reaction. The reaction temperature was maintained at 60° C. Ethyl acetate (1.5 g) was added to the polymer solution every 30 minutes until the conversion of isooctyl acrylate to polymer reached a minimum of 95%, typically 20–30 hours. An additional charge of Lucidol 75 (0.07 g) premixed with ethyl acetate (3.0 g) was added after 5 hours and nine hours reaction time. When 95% minimum reaction conversion was achieved, the resulting polymer solution was diluted with heptane to 20–23%, solids, cooled and drained. The inherent viscosity in ethyl acetate at 0.15 g/dl was measured at 1.7–2.0 dl/g. The inherent viscosity was measured by conventional means using a Canon-Fenske #50 viscometer in a water bath controlled at 27° C. to measure the flow time of 10 milliliters of the polymer solution. The test procedure and apparatus are described in detail in "Textbook of Polymer Science", F. W. Billmeyer, Wiley Interscience, Second Edition, 1971, pages 84 and 85.

Preparation of "Dried" Adhesive

Dried adhesive was prepared by coating a solution of the adhesive copolymer at a thickness of 500 µm onto a release liner. The coated release liner was oven dried to remove solvent and reduce the amount of residual monomers. The dried adhesive was stripped off the release liner and stored in a container.

Preparation of Multidirectional Polypropylene Backing

A spunbonded polypropylene nonwoven web with an offset intermittent spot welded structure and a basis weight of a nominal 60 grams per square meter (available as LUTRASIL® LS-4460 from Freudenberg Spunweb Co.) was heated (about 138° C.) and stretched under tension (accomplished by adjusting the unwind and wind-up tensions or speeds to produce a 1:1.5 (±0.1) differential) using conventional equipment in a process known as "necking down" or "stretch-setting". This process reduced the width of the web, increased the length of the web and imparted a stretch in the cross-web direction. The "necked down" web was then microcreped using a MICROCREPER™ (available from the MICREX Corp., Walpole, Mass., USA) with compression ratios from 30% to 40% and a temperature set at 70° C. This process imparted a stretch in the down-web or machine direction. The resulting multidirectional stretch web was calendered on conventional equipment at a temperature of about 138° C. and a pressure of 100 psi (7.0 Kg/cm$^2$) using a smooth rubber top roll and a smooth chrome bottom roll with a set gap of 0.005" (0.0127 cm) to produce a smoother surface for lamination of the drug-in-adhesive matrix while retaining the multidirectional stretch properties.

Preparation of a Flurbiprofen Transdermal Delivery Device

A solution of vinylpyrrolidone-vinyl acetate copolymer (201.34 g of Kollidon VA 64) in isopropanol (2684.1 g) was added to a solution containing isopropyl myristate (862.7 g), S(+)-flurbiprofen (201.28 g), and adhesive (1610.3 g of dried 90/10 isooctyl acrylate/acrylic acid copolymer) in a mixture of ethyl acetate (5155 g) and isopropanol (1288.5 g) to afford a homogeneous coating formulation. The formulation was coated through an extrusion die onto a release liner (3M Scotchpak™ 1022 Release Liner). The coated release liner was oven dried for 10 min with the following temperature program : first heating zone at 65° C., second heating zone at 75° C., and third heating zone at 90° C. The polypropylene backing prepared above was corona treated then laminated to the coated liner. The resulting laminate had a drug loading of 0.7 mg/cm$^2$. The laminate was die cut into 1.55 cm$^2$ patches. Penetration through hairless mouse skin was determined using the test method described above. The results are shown in Table 1 below where each value is the average of nine independent determinations. Penetration through human cadaver skin was determined using the test method described above. The results are shown in Table 2 below where each value is the average of five independent determinations.

The tack was measured using ASTM D-2979-71 and found to be 143.60 g/cm$^2$ (average of ten independent determinations).

The adhesion on steel was measured using the test method described above and found to be 2.33 Newton (average of seven independent determinations).

TABLE 1

| | Hairless Mouse Skin Penetration | | |
|---|---|---|---|
| Example | Cumulative Amount Penetrating (µg/cm$^2$) | | |
| Number | 12 hour | 24 hour | 48 hour |
| 7 | 73.52 | 151.32 | 290.02 |

TABLE 2

| | Human Cadaver Skin Penetration | | |
|---|---|---|---|
| Example | Cumulative Amount Penetrating (µg/cm$^2$) | | |
| Number | 12 hour | 24 hour | 48 hour |
| 7 | 32.63 | 63.28 | 112.18 |

The data in Tables 1 and 2 show that a device according to the invention has a high flux rate and is suitable for delivering flurbiprofen through skin.

Moisture Vapor Transmission Rate

The moisture vapor transmission rate of the transdermal delivery device prepared above was determined using the test method described above and was found to be 442 g/m²/24hr. Accordingly, the device is nonocclusive.

What is claimed is:

1. A drug delivery device comprising a flexible backing having on at least one part of one surface thereof a carrier comprising a drug, said flexible backing comprising a nonwoven thermoplastic polymer web having multidirectional elasticity comprising substantially continuous and randomly deposited, molecularly oriented fibers of thermoplastic polymer bonded together at intermittent patterned areas of the web with unbonded spans of fibers between the bond areas, the fibers being heat set in an undulating configuration with respect to the basic plane of the web to form a series of repeating crests and valleys in the machine direction which flatten into the basic plane on strain induced elongation of the web in the machine direction and reassume their undulated configuration on strain release to provide substantially complete elastic recovery in the machine direction up to at least about 10% strain, the web also containing unbonded spans of fibers disposed in non-linear, buckled configuration with respect to the cross direction in the basic plane and heat set therein such that, on strain induced elongation up to at least about 10% in the cross direction, fibers align in the cross direction and, on strain release, substantially spontaneously reassume their non-linear, buckled configuration, the patterned areas occupying less than about 50% of the surface area of the web and distributed in a density of about 8 to 490/cm².

2. A drug delivery device according to claim 1 wherein said carrier comprises an adhesive composition.

3. A drug delivery device according to claim 1 wherein said thermoplastic polymer is a thermoplastic polyolefin or a thermoplastic polyester.

4. A drug delivery device according to claim 3 wherein said thermoplastic polyolefin is a polypropylene.

5. A drug delivery device according to claim 1 wherein said surface of said flexible backing comprising said carrier is smoother than the surface of said flexible backing opposite thereto.

6. A drug delivery device according to claim 2 wherein said adhesive composition further includes a penetration enhancer.

7. A drug delivery device according to claim 1 wherein said drug delivery device is a transdermal drug delivery device.

8. A drug delivery device according to claim 7 wherein said drug is an anti-inflammatory.

9. A drug delivery device according to claim 2 wherein said drug delivery device has a moisture vapor transmission rate of more than about 400 g/m²/24hr.

10. A drug delivery device according to claim 1 wherein said surface of said flexible backing comprising said carrier is corona treated.

* * * * *